United States Patent [19]
Baskent et al.

[11] 4,400,327
[45] Aug. 23, 1983

[54] PREPARATION OF SILOXYLATED METAL-CONTAINING CATALYSTS

[75] Inventors: Feyyaz O, Baskent, Mahopac, N.Y.; James D. Reedy, New Fairfield, Conn.

[73] Assignee: Union Carbide Corporation, Danbury, Conn.

[21] Appl. No.: 335,612

[22] Filed: Dec. 30, 1981

[51] Int. Cl.$^3$ .............................. C07F 7/22; C07F 7/24; C07F 3/10; C07F 3/06
[52] U.S. Cl. .......................... 260/429 R; 252/431 R; 260/429.2; 260/429.5; 260/429.7; 260/429.9; 260/431; 260/435 R; 260/438.1; 260/439 R; 564/215
[58] Field of Search ............. 260/429.7, 429.5, 429 R, 260/404, 435, 431, 438.1, 439 R, 429.9, 429.2; 252/431 R; 564/215

[56] References Cited

U.S. PATENT DOCUMENTS

| | | | |
|---|---|---|---|
| 2,872,168 | 3/1975 | Collman et al. | 564/215 X |
| 3,681,266 | 8/1972 | Domba | 260/404 X |
| 3,919,276 | 11/1975 | Le Grow et al. | 564/215 |
| 3,927,052 | 12/1975 | Vizurraga | 260/429.7 |
| 3,993,606 | 11/1976 | Von Bonin | 260/2.5 AH |
| 4,038,221 | 7/1977 | Koster | 260/2.5 AH |
| 4,152,343 | 5/1979 | Wohlfarth et al. | 260/429.7 |

Primary Examiner—Helen M. S. Sneed
Attorney, Agent, or Firm—Paul W. Leuzzi, II

[57] ABSTRACT

Reaction of silylamine with a metallic carboxylate produces siloxylated organometallic compounds with M—O—Si bonds. These siloxylated organometallic compounds are useful catalysts in the preparation of urethane foams and elastomers, especially when prepared in situ with the urethane foam or elastomer reactants.

9 Claims, No Drawings

PREPARATION OF SILOXYLATED METAL-CONTAINING CATALYSTS

BACKGROUND OF THE INVENTION

This invention generally relates to a novel process for preparing siloxylated metal-containing catalysts and their use in the preparation of urethane foam and elastomers. More particularly, the invention relates to the reaction between silylamines and metallic carboxylates to produce the siloxylated organometallic catalysts.

The prior art discloses two common ways of forming siloxylated metallic bonds:

$$R_3SiONa + ClM \rightarrow R_3SiOM + NaCl \quad (1)$$

$$\equiv SiOAc + ROM \rightarrow \equiv SiOM + ROAC \quad (2)$$

Although (1) is a fast and complete reaction, it is necessary to remove the sodium chloride since halides are poisonous to many metal catalysts. Also, the sodium silanolate is such a strong base that it can cause unwanted side reactions prior to forming the silanolates or subsequent side reactions due to slight stoichiometric excesses. The reaction designated (2) is generally too slow at temperatures below 100° C. to form siloxylated metallic bonds in situ in urethane reactants. Also this reaction lacks general utility because the temp. necessary for M—O—Si formation is sufficiently high to disproportionate M—O—Si to M—O—M and Si—O—Si, thus catalytic activity would be lost.

In some urethane applications the ideal catalyst system is one in which the active catalyst is formed in the desired time frame in situ. Since in urethane processing there are always multiple components, time is needed to mix the reactants thoroughly and transport them to a mold before reactants start forming high viscosity products.

Previously, U.S. Pat. No. 4,038,221 taught a process for open-celled HR foams utilizing a silicon compound in combination with organometallic catalysts. However, siloxylated metal-containing materials are not disclosed.

With respect to the use of the siloxylated organometallic catalyst, U.S. Pat. No. 3,993,606 disclosed a process for manufacturing a foam having good mold release characteristics. However, the silicone containing compound has Si—CH₂—N linkages which are too stable to readily react with the metallic material to form siloxylated metallic bonds.

Other references of interest include German Pat. No. 2,524,000 describing silicon-tin compounds as effective condensation catalysts; German Pat. No. 2,404,399 disclosing siloxane compositions and tin as release coatings; German Pat. No. 2,259,802 teaching rebound plastic siloxanes obtained by reacting siloxane in presence of tin carboxylatediethoxydimethylsilanes; USSR Pat. Nos. 509,620 and 319,621 concerning the hardening of the polymeric materials in presence of organostannosiloxanes; and J. Amer. Chem. Soc., 81, 975(1959) which discloses the preparation and properties of some silylalkyl substituted tin compounds.

The prior art, as a whole, does not teach, disclose or suggest the novel process of the present invention which is capable of readily producing siloxylated metal-containing catalysts. The fact that metallic carboxylates of low activity can be mixed with silylamines in situ to form an active siloxylated metallic bond is valuable in that very little reaction is preferred until the mold has been filled at which point very rapid cure is necessary. The siloxylated metal-containing catalysts of the present invention fulfill this criteria.

SUMMARY OF THE INVENTION

The present invention provides a novel process for preparing siloxylated metal-containing catalysts and their use in the preparation of urethane foams and elastomers. The process entails reacting a silylamine of the formula:

$$R_{4-n}Si(NR'R'')_n$$

wherein R is an alkyl, alkaryl, alkenyl, alkynyl, aryl, cycloaliphatic, siloxy or heteroatom substituted aliphatic, group; R' and R'' are individually hydrogen, alkyl, alkaryl, alkenyl, alkynyl, aryl, cycloaliphatic or heteratom substituted aliphatic, groups provided R' and R'' cannot both be hydrogen; and n is one to four inclusive, with a metallic carboxylate of the formula:

$$M(OCOR''')_xR_y''''$$

wherein M is a metal with an oxidation state, R''' and R'''' are individually an alkyl, alkaryl, alkenyl, alkynyl, aryl, cycloaliphatic or heteroatom subtituted aliphatic aryl group; x is at least one but no more than the oxidation state of M and y is equal to the oxidation state of M minus x, to form a siloxylated metal-containing catalyst.

The siloxylated metal-containing catalyst so formed is employed in the preparation of urethane foams and elastomers.

DETAILED DESCRIPTION OF THE INVENTION

In accordance with the present invention there is provided a novel process for producing siloxylated metal-containing catalysts having M—O—Si bonds. The process entails a reaction between silylamine with a metallic carboxylate.

Suitable silylamines are represented by the formula:

$$R_{4-n}Si(NR'R'')_n$$

wherein R,R',R'' and n are of the same significance as previously set forth. Useful silylamine include, but are not limited to,

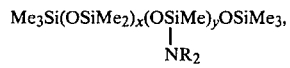

N,N-dimethylaminotrimethylsilane, N,N-dimethylaminotricyclohexylsilane, N,N-ethylhexylaminotripropylsilane, bis-[N,N-diheptylamino]diphenylsilane, bis-(N,N-dioctylamino)dioctylsilane, tris-(N,N-dimethylamino)propylsiloxysilane, tetra kis-(N,N-dimethylamino)silane, N,N-dibutyl-aminotrioctadecylsilane, and N,N-octylhexylaminotrimethylsilane, R, R' and R'' should contain no more than twenty-four carbon atoms, preferably no more than twelve carbon atoms and most preferred a methyl group. It is also preferred that R, R' and R'' are alkyl groups and that the value of n be one. The preferred silylamine is N,N-dimethylaminotrimethylsilane.

Suitable metallic carboxylates are represented by the formula:

$$M(OCOR''')_xR''''_y$$

wherein M,R''',R'''',x and y are all of the same significance as previously set forth. Useful metallic carboxylates include, but are not limited to, dibutyltin diacetate, dibutyltin dilaurate, mercury(II) diacetate, lead(II) acetate, stannous dioctoate, titanium tetraacetate, iron (II) octoate, cerium (III) octoate, and zinc octoate. R''' and R'''' should contain no more than twenty-four carbon atoms, preferably no more than twelve.

The metals useful as metallic carboxylates include all metals known to form silanolates. Generally, this class will include the metals of groups IB, IIB, IIIB (including the lanthamide and actinide series), IVB, VB, VIB, VIIB, VIII as well as gallium, indium, thallium, germanium, tin and lead. Most preferably, the metals are selected from the group consisting of iron, tin, lead, titanium, cerium and mercury.

In carrying out the reaction between the silylamine and the metallic carboxylate, it is recommended that the reaction temperature be kept below the point where significant formation of Si—O—Si and M—O—M bonds occur. For the less stable silanotates this is at or below room temperature, for the more stable silanolates it is about 100° C., with a few, such as titanium being significantly higher. It is also recommended that with respect to any substituted or unsaturated groups employed, that they are chosen so as not to be deleterious in their interaction to the Si—N bond of the silylamine or the Si—O—M bond of the final product and that they do not adversely affect the thermal stability of the reactants.

The catalyst of the present invention has been shown to produce acceptable quality, cure and the desired cream-rise profiles in foams such as high resiliency, flexible and rigid polyurethane foam, polyester foam and reaction injection molding of urethane elastomers. Furthermore, these catalysts have been found to be excellent latent cure catalysts for high resilience foam systems (HR foams).

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

Table A shows the enhanced urethane catalysis using metal carboxylates in the presence of silylamines. In some cases, the reactivity improved by several orders of magnitude.

The urethane reactants for this study were a glycerine-started polyol which was terminated by secondary hydroxyl groups and toluene diisocyanate (80/20). The polyol contained about 85% oxypropylene units and 15% internal oxyethylene units and had a hydroxyl number of 46.

In some cases, there is only a small amount of MOSi formed yet there are large rate enhancements in urethane catalysis. Table A contains examples where metals which are considered totally inactive are activated to the extent of commercial urethane catalysts. In several cases the acetate salts could not be activated with silylamines but octoates could. A potential side reaction is the silylation of the hydroxyl groups of the polyol with the silylamine but we were not able to detect any products of this type.

TABLE A

Effect of Silylamine on Transition Metal Salts as Polyurethane Catalysts (55° C. Initiation)

| Metal Salt | Grams of Metal Salt Per 100 Grams Polyol | Gel Times (Min.) Parent Salt | Parent Salt with Silylamine 2.4 cc |
|---|---|---|---|
| Control | 0 | None | >960 |
| Mn(-OCOC$_7$H$_{15}$)$_2$(6% Mn) | 1.5 | 8 | 1.5 |
| Fe(-OCOC$_7$H$_{15}$)$_2$(10.5% Fe) | 0.9 | 4 | 0.3 |
| Co(-OCOC$_7$H$_{15}$)$_2$ | 0.75 | 5 | 1 |
| Ni(-OCOC$_7$H$_{15}$)$_2$ | 0.5 | >960 | 13 |
| Co(OCOCH$_3$)$_2$ | 1.0 | >960 | 20 |
| Rare Earth Octoate (6% RE) | 1.5 | 12 | 1 |
| Rare Earth Neodecanoate (6% RE) | 1.5 | 60 | 2 |
| Ce(-OCOC$_7$H$_{15}$)$_3$(12% Ce) | 0.75 | 180 | 3 |
| Sn(-OCOC$_7$H$_{15}$)$_2$ | 0.15 | 0.5 | 0.3* |
| Bu$_2$Sn(-OCOC$_{11}$H$_{23}$)$_2$ | 0.09 | 2 | 0.5* |
| Zn(-OCOC$_7$H$_{15}$)$_2$ | 0.09 | >960 | 6* |
| Ni(-OCOCH$_3$)$_2$·4H$_2$O | 0.12 | >960 | >960* |

*The amount of Me$_3$Si N Me$_2$ used was 1.77 g/100 g polyol

SILOXYLATED METAL CATALYST PREPARATION

EXAMPLE I

Preparation of Dibutyl-bis-(trimethylsiloxy)stannane Bu$_2$Sn[OSi(CH$_3$)$_3$]$_2$ Reaction:

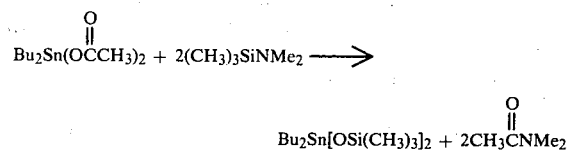

Into a 500 cc, 3-necked flask, equipped with thermometer, thermo-watch, mechanical stirrer and reflux condenser, 59.98 grams (0.168 mole) of dibutyl tin diacetate and 46.2 grams (0.395 mole) (xs amount) N, N-dimethylaminotrimethylsilane were charged. The resulting mixture was heated to 80° C. for two hours. Dibutyl-bis-trimethysiloxy stannane was distilled at 100° C./0.3 mm Hg. $^1$H nmr of the product showed a ratio 1:1 for butyl and methyl hydrogens. A side product was collected and identified as N,N-dimethylacetamide. Using vapor phase chromatography (Vpc), ir and nmr Vpc, ir and nmr ($^1$H, $^{119}$Sn) scans of bis-trimethylsiloxydibutyl stannane and N,N-dimethylacetamide were consistent with the proposed structures.

$^{119}$Sn nmr, showed a single peak which was shifted to lower field compared to starting material dibuyltin diacetate. The shift to lower field is consistent with bonding of tin to —Si or —OSi.

Elemental analysis of this product is shown below:

| Structure | | % C | % H | % S | % Si |
|---|---|---|---|---|---|
| (Bu)$_2$Sn(OSiMe$_3$)$_2$ | Calc.: | 40.88 | 8.76 | 28.96 | 13.62 |
| | Found: | 41.09 | 8.57 | 29.32 | 13.7 |

This product will be referred to as "A" in subsequent discussion.

EXAMPLE II

Reaction of Dimethylamino-Terminated Dimethylsilicone with Dibutyltin Dilaurate

A. $Bu_2Sn-O(Me_2SiO)_xSiMe_2O-SnBu_2$     (IV)

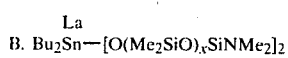

B. $Bu_2Sn-[O(Me_2SiO)_xSiNMe_2]_2$     (V)

AB Type

La = Laurate

Reaction:

x mole $Bu_2Sn(La)_2$ + y mole $Me_2N(Me_2SiO)_xSiMe_2NMe_2 \xrightarrow{\Delta}$ Product (A) or (B)

Based on moles of dibutyltin dilaurate either product (A) dibutyltin laurate endblocked dimethylsilicone (ABA type) or product (B) AB type product could be synthesized.

Based on desired structure (A) or (B), known amounts of dimethylamino terminated dimethylsilicone and dibutyltin diluarate were charged into a 3-neck, 500 cc flask equipped with reflux condenser, thermometer, thermowatch and mechanical stirrer under nitrogen blanket. The mixture was heated to 80° C. and held for two hours. The resulting product is clear and light straw color. Vpc analysis showed the presence of dimethyllaurylamide and the I.R. spectra were consistent with predictions for $-Me_2SiOSnBu_2$-compounds.

This product will be referred to as "B".

EXAMPLE III

The Reaction of N,N-dimethylaminotrimethylsilane with Mercury (II) acetate

Reaction:

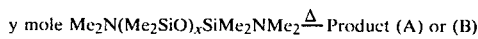

$Hg(OCCH_3)_2 + 2(H_3C)_2NSi(CH_3)_3 \xrightarrow{\Delta} Hg[OSiCH_3]^*_2 +$ $$\underset{\underset{2CH_3CN(CH_3)_2}{\|}}{O}$$

Reaction:

$(CH_3)_2NSiMe_2(Me_2SiO)_4SiMe_2NMe_2 + 1.5$ mole $Bu_2Sn(OCCH_3)_2$  $\xrightarrow{\Delta}$ $(CH_3)_2NSiMe_2(Me_2SiO)_4SiMe_2OSnBu_2 + CH_3CN(CH_3)_2OCCH_3$

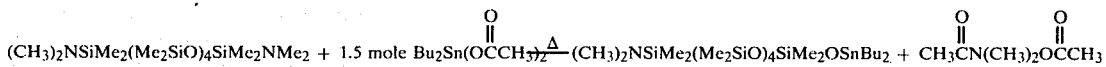

*This reaction does not go to completion, thus the product contains some mono-siloxated product and unreacted $Me_2NSiMe_3$.

Into a 500 cc, 3-necked flask, equipped with thermometer, thermowatch, mechanical stirrer and reflux, condenser, 28.8 grams (0.0904 mole) of mercury (II) acetate and 21.2 grams (0.1807 mole) (xs amount) N,N-dimethylaminotrimethylsilane and 50 grams of THF were charged. The resulting mixture was heated to 80° C. for two hours at which time it was amber and homogenous. It was then allowed to cool to room temperature. Dimethylacetamide was detected in the product and the presence of product was inferred by reaction stiochometry and increased catalytic activity.

This product will be referred to as "C".

EXAMPLE IV

Reaction of N,N-dimethylaminotrimethylsilane with Lead (II) Acetate

Reaction:

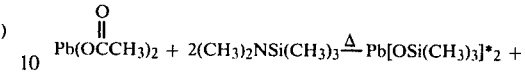

$Pb(OCCH_3)_2 + 2(CH_3)_2NSi(CH_3)_3 \xrightarrow{\Delta} Pb[OSi(CH_3)_3]^*_2 +$

$2CH_3CN(CH_3)_2$

EXAMPLE V

The reaction of N,N-Dimethylaminotrimethylsilane with Dibutyltindilaurate (2:1 mole)

Into a 500 ml, 3-necked flask were charged 81.2 grams (0.694 mole) of N,N-Dimethylaminotrimethylsilane), 218.9 grams (0.347 moles) of dibutyltin diluarate. The flask was equipped with a thermometer, mechanical stirrer and condenser. The mixture was heated under a nitrogen blanket at 60° C. A exotherm of 10° C. was detected. The product is straw color, clear liquid.

Reaction:

$Bu_2Sn(OC(CH_2)_{10}CH_3)_2 +$ $2(CH_3)_2NSi(CH_3)_3 \xrightarrow{\Delta} Bu_2Sn[OSi(CH_3)_3]_2 + CH_3(CH_2)_{10}CN(CH_3)_2$

This product will be referred to as "E".

EXAMPLE VI

Reaction of a Dimethylaminoterminated Dimethylsilicone Fluid with Dibutyltindiacetate Into a 500 ml, 3-necked flask were charged 41.9 grams (0.20 mole) dimethylamino terminated dimethylsilicone fluid and 58.1 grams (0.165 moles) of dibutyltindiacetate. Upon addition of the ingredients, the mixture exothermed to a peak temperature of 52° C. It was then heated to 65° C. and held for two hours. The product was a clear, light yellow liquid.

This product will be referred to as "F".

EXAMPLE VII

The Reaction Between N,N-Dimethylaminotrimethylsilane and Dibutyltindilaurate (1:1 mole)

Reaction:

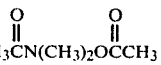

$Bu_2Sn(OC(CH_2)_{10}CH_3)_2 +$

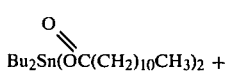

-continued
Reaction:

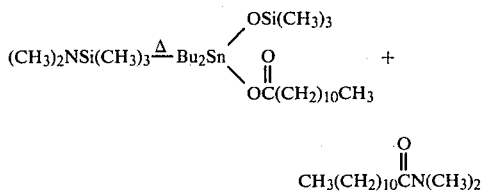

$$CH_3(CH_2)_{10}\overset{O}{\overset{\|}{C}}N(CH_3)_2$$

Into a 500 ml, 3-necked flask equipped with condenser, mechanical stirrer and thermo-watch, were charged 40.0 grams (0.342 mole) N,N-dimethylaminotrimethylsilane, and 215.6 grams (0.342 mole) dibutyltin dilaurate. The exotherm was to 60° C.; the solution was kept at that temperature for two hours, then cooled.

This product will be referred to as "G".

EXAMPLE VIII

Reaction of N,N-dimethylaminotrimethylsilane with Stannous Octoate (2:1 mole)

Into a 500 ml, 3-necked flask equipped with condenser, machanical stirrer and thermo-watch were charged 18.3 grams (0.157 mole) of dimethylaminotrimethylsilane and 31.68 grams (0.078 mole) stannous octoate. The exotherm was to 60° C.; the solution was kept at that temperature for two hours. The product was homogenous and had a very light straw color.

Reaction:

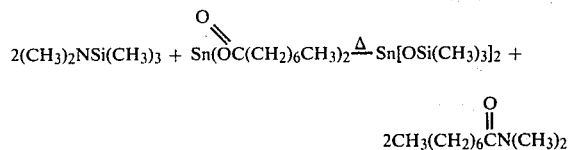

$$2CH_3(CH_2)_6\overset{O}{\overset{\|}{C}}N(CH_3)_2$$

This product will be referred to as "H".

EXAMPLE IX

Reaction of N,N-Dimethylaminotrimethylsilane with Stannous Octoate (1:1 mole)

Into a 500 ml, 3-necked flask were charged 11.21 grams (0.096 mole) stannous octoate. The reaction vessel was equipped with a condenser, mechanical stirrer and thermowatch. The reaction exotherm reached 60° C. and this temperature was maintained for two hours. The clear product was allowed to cool.

Reaction:

$(CH_3)_3SiN(CH_3)_2 +$

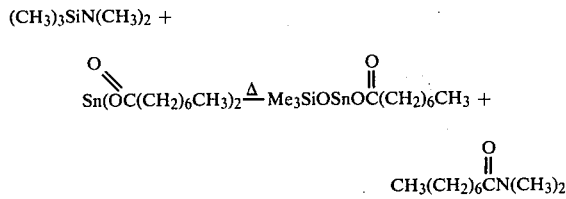

$$CH_3(CH_2)_6\overset{O}{\overset{\|}{C}}N(CH_3)_2$$

This product will be referred to as "I".

EXAMPLE X

Reaction of Dibutyltindiacetate with tris-Dimethylaminosilane

Dibutyltin diacetate, 89.71 grams (0.256 mole) was placed into a 200 cc, 3-necked flask equipped with a thermometer, magnetic stirrer and an addition funnel. Tris-dimethylaminosilane 10.6 grams (0.066 mole) was placed into the addition funnel and then slowly added to the flask. There was a exotherm in which the solution temperature increased from 27° to 61° C. The clear product was then cooled.

Reaction:

$$4Bu_2Sn(\overset{O}{\overset{\|}{O}CCH_3})_2 +$$

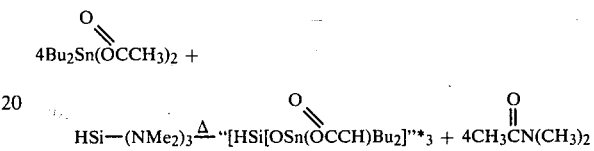

*Actually numerous SiOSn products are formed.

This product will be referred to as "J".

HIGH RESILIENCY FOAM PROCEDURE

A mold is prepared by waxing lightly with Brulin Peramold Realease Agent and heating the mold in 140° C. oven for about ten minutes (175°–200° F.). Excess mold-release is wiped off and the mold is allowed to cool to 120° F. before foaming. The initial mixing is started when mold temperature is about 130° F. Preheating mold to the higher temperature is necessary to remove solvent from the mold release agent and no more mold release is used with subsequent foams until sticking occurs making foams difficult to de-mold.

All components except the isocyanate are measured or weighed into a one-half gallon, five-inch diameter, cylindrical, cardboard carton and mixed 60 seconds with a two and one-half inch, six-blade turbine at 4000 RPM. Isocyanate is weighed into the mix, stainless steel baffles designed for the one-half gallon are inserted, and mixing is continued for five seconds. The carton is then lowered to allow the mixer to drain while observing the cream time, and the contents are quickly poured into the mold. The mold lid is closed and clamps are placed around mold to prevent flash-out. Exit time is observed as the time when all four top holes are full, and pop time as the time when extruded parts stop bubbling.

The four-inch mold is de-molded after ten minutes at room temperature. The foam sample is trimmed around edges with scissors and weighed before crushing cells open and allowed to cure for three days at room temperature before testing.

Also for the sake of brevity, the following designations are used to denote various processing conditions and evaluation determinations of the foams produced in the examples and are defined as indicated below:

1. Cream Time (seconds)—Denotes the time in seconds it takes for the foam-forming mixture to go from a homogeneous clear liquid to a heterogenous milky liquid.

2. Rise Time (seconds)—Denotes the time in seconds it takes a foam to reach its maximum height.

3. Gel Time (seconds)—Denotes the time in seconds it takes a foam to reach sufficient strength to be handled.

4. Activator Solubility—Denotes the solubility of a aqueous premixture of amine catalyst and surfactant foam stabilizer.

5. Breathability—Denotes the porosity of a foam, being roughly proportional to the number of open cells in a foam, and was measured in accordance with the NOPCO breathability test procedure described by R. E. Jones and G. Fesman, *Journal of Cellular Plastics*, January, 1965. It is a measure of the air flow through a two inch by two inch by one inch foam sample expressed as standard cubic feet per minute (SCFM).

6. Density (pcf)—Denotes the density of a foam in pound per cubic foot.

7. ILD (pounds per 50 square inches)—Denotes an indentation rating of how much force (load in pounds per 50 square inches) is necessary to compress a foam sample at various deflections.

8. Compression Set (percent)—Denotes the degree of failure of a foam sample to return to its original size after removal of a deforming force. The permanent change in height of the foam sample is measured and the percent set calculated.

9. Tensil Strength (psi)—Denotes the force necessary to rupture a foam specimen when stretched to the breaking point divided by the original cross sectional area given in pounds per square inch.

TABLE I

| Foam | Control | 1 | 2 | 3 |
|---|---|---|---|---|
| Polyol A | 60 | → | → | → |
| Polyol B | 40 | → | → | → |
| Water | 2.6 | → | → | → |
| Bis (dimethylaminoethyl) ether as 70% solution in dipropylene glycol | 0.1 | → | → | → |
| Triethylenediamine | 0.12 | → | → | → |
| Dibutyltindilaurate | 0.015 | → | → | → |

TABLE I-continued

| Foam | Control | 1 | 2 | 3 |
|---|---|---|---|---|
| Surfactant A | 1.0 | → | → | → |
| TDI 80/20 | 104 Index | → | → | → |
| Experimental Catalyst | — | B | B | C |
| Concentration | — | 0.25 | 0.75 | 1.0 |
| Comments: | Collapse | good foam | → | → |
| Cell Structure: | — | excellent desired high resilience urethane structure. | → | → |

Polyol A — 5000 M wt triol, OH number 34, ethylene oxide content = 16%, Primary OH = 75%
Polyol B — by weight 80/10/10: polyol containing 10% styrene OH number 34, 10% acrylonitrile grafted dispersion, with a final OH number 28
Surfactant A — non-hydrolyzable silicone surfactant
TDI 80/20 — tolyene diisocyanate 80/20 2,4-,2,6 isomer ratio

TABLE II

| Foam | 4 | 5 | 6 | 7 | 8 |
|---|---|---|---|---|---|
| Polyol A | 60 | → | → | → | → |
| Polyol B | 40 | → | → | → | → |
| H₂O | 2.6 | → | → | → | → |
| Amine Catalyst AA | 0.1 | → | → | → | → |
| Amine Catalyst BB | 0.3 | → | → | → | → |
| Dabco 33LV | 0.4 | → | → | → | → |
| Diethanolamine | 0.6 | → | → | → | → |
| Surfactant A | Varied | → | → | → | → |
| Dibutyltindilaurate | 0.1 | → | → | → | → |
| TDI 80/20 | 104 Index | → | → | → | → |
| Experimental Catalyst C | — | 0.05 | 0.075 | 0.1 | 0.15 |
| ILD 25% | 33 | 61 | 55 | 53 | 40 |
| 65% | 80 | 136 | 130 | 133 | 90 |
| Return 25% | 27 | 42 | 37 | 32 | 32 |
| Comfort factor: | 2.4 | 2.3 | 2.4 | 2.51 | 2.3 |
| % ball rebound: | 60 | 65 | 64 | 60 | 58 |
| Comments: | Control | Accceptable foam | → | → | |

Amine Catalyst AA: 70% bis (2-dimethylaminoethyl) ether solution in dipropylene glycol
Amine Catalyst BB: 33.3% 3-dimethylamino-N,N—dimethylpropanol and 66.6% tergitol TP-9.

TABLE III

Evaluation of Metallosiloxane Catalyst in H.R. Foams

| Foam | 6 | 7 | 8 | 9 | 10 | 11 | 12 | 13 |
|---|---|---|---|---|---|---|---|---|
| Polyol A | 60 | → | → | → | → | → | → | → |
| Polyol B | 40 | → | → | → | → | → | → | → |
| H₂O | 2.6 | → | → | → | → | → | → | → |
| Amine Catalyst AA | 0.05 | → | → | → | → | → | → | → |
| Amine Catalyst BB | 0.3 | → | → | → | → | → | → | → |
| 33% TEDA | 0.35 | → | → | → | → | → | → | → |
| Surfactant A | 1.5 | → | → | → | → | → | → | → |
| Tolylene Diisocyanate (80/20 2,4-,2,6 isomer ratio) | 100 index | → | → | → | → | → | → | → |
| Experimental Catalyst | — | — | — | "E" 0.0075 | → 0.015 | "G" 0.0075 | → 0.015 | → 0.022 |
| Mold exit time (sec) | 98 | 62 | 60 | 59 | 60 | 68 | 62 | 60 |
| ILD's lbs/50 in²: | | | | | | | | |
| 25% | 26 | 26 | 23 | 29 | 28 | 30.5 | 30 | 23 |
| 65% | 72 | 72.5 | 78.5 | 86 | 76.5 | 84 | 81 | 78 |
| 25% | 24 | 0.5 | 18 | 24.5 | 23 | 25 | 24 | 19 |
| Comfort factor | 2.76 | 2.79 | 3.11 | 2.83 | 2.75 | 2.75 | 3.70 | 3.30 |
| Comments | low tear property slow pop-out time | Acceptable shrinkage | shrinkage | Acceptable | → | → | → | |

| Foam | 14 | 15 | 16 | 17 | 18 | 19 | 20 |
|---|---|---|---|---|---|---|---|
| Polyol A | 60 | → | → | → | → | → | → |
| Polyol B | 40 | → | → | → | → | → | → |
| H₂O | 2.6 | → | → | → | → | → | → |
| Amine Catalyst AA | 0.05 | → | → | → | → | → | → |
| Amine Catalyst BB | 0.3 | → | → | → | → | → | → |
| 33% TEDA | 0.35 | → | → | → | → | → | → |
| Surfactant A | 1.5 | → | → | → | → | → | → |
| Tolylene Diisocyanate (80/20 2,4-,2,6 isomer ratio) | 100 index | → | → | → | → | → | → |
| Experimental Catalyst | "C" 0.0025 | → .003 | → 0.005 | → 0.0075 | "D" 0.005 | → 0.0075 | → 0.015 |

TABLE III-continued

| Evaluation of Metallosiloxane Catalyst in H.R. Foams | | | | | | | |
|---|---|---|---|---|---|---|---|
| Mold exit time (sec) | 78 | 73 | 69 | 64 | 70 | 68 | 63 |
| ILD's lbs/50 in$^2$: | | | | | | | |
| 25% | 33 | 31 | 35 | 33 | 34 | 31 | 37 |
| 65% | 82 | | 79 | 79 | 78 | 76 | 80 |
| 25% | 28 | | 29 | 27 | 27 | 25 | 30 |
| Comfort factor | 2.5 | | 2.16 | 2.4 | 2.34 | 2.45 | 2.25 |
| Comments | | shrinkage | Acceptable | → | → | → | → |

33% TEDA — 33 wt % triethylenediamine and 66 wt % dipropylene glycol
AFPI — polymethylene polyphenol isocyanate polymer containing 2.6–2.9 moles of NCO/mole of polymer and having 31.4% isocyanate content All of the catalyst of this invention produced good quality HR molded and free-rise foams. Furthermore, these catalyst could be prepared in-situ and have the same affect on foam properties.

Some of these products were evaluated in HR foam (formulation is shown in Table II). In Table III ILD and support factors for the foams which are made with siloxylated metal catalyst are shown.

HR properties of the foams made with in-situ formation of metal catalyst were generally excellent. Load bearing properties were high (~50 lbs/in$^2$ at 25Δ ILD) and SAC factors were approximately 2.4. Use levels of the product were varied from 0.05 to 0.5 pts. The foam in general were tight but did not have any shrinkage. Resiliency values were around 60 percent.

Metallosiloxanes were evaluated in HR foam (formulation is shown in Table III) and their use level has been varied. Physical properties (i.e. load properties) and gel times are shown in Table III. Foam 6 is the control foam without any metal-containing catalyst. The reactivity of the system was decreased considerably (shown by longer pop-out or mold-fill times). At the de-mold tear properties of the foam were low.

Experimental metallosiloxanes decrease the exit time (indicative of speeding of the reaction) and improves the tear properties and de-mold characteristics (Foams No. 9 thru No. 20). At high dibutyltindilaurate use levels, there was produced foams with shrinkage (Foam No. 8). However, experimental catalyst at same use levels as the control produced foams without any shrinkage (foams Nos. 10, 12, and 20).

The load properties of foam with experimental material was increased at least 10% over the control foams.

RIGID URETHANE FOAMS WITH STANNOSILOXANE CATALYSTS

The catalysts of this invention may also be employed as the only catalyst used to prepare rigid polyurethane foam or may be employed as a component of a catalysts mixture as illustrated below.

In order to prepare the rigid foams a one-quart carboard cup is charged with a premix of polyol and fluorocarbon blowing agent. The mixture was blended with ether blade, attached to drill press, spinning at 2000 rpm for a period of 10 seconds. Without interrupting the mixing, a premix of the isocyanate and a surfactant was rapidly added over a 4 second perid. Stirring was continued for an additional 4 seconds, then stopped and the formulation was poured into an 8"×8"×6" cardboard box. The cream time was defined as the point where the first small bubbles of trapped gas are observed on the surface of the foaming mixture. This usually appears as a lightening in the color of the resinous material from dark brown to beige. As the foam was rising, a clean metal spatula is inserted into the foam and withdrawn. The spatula is then wiped clean and this process is repeated until fine strands of the forming polymer can be drawn out of the foam with the spatula. The time at which these threads of urethane first appear is called the gel or gelation time. After the gel time has been measured the surface of the foam is touched lightly with a finger to determine when the surface is "tack-free." Initially the foam surface collapses when touched leaving a deposit of resinous polymer on the finger. The finger is wiped clean and the procedure is repeated until the foam may be touched without breaking the skin of the foam or leaving a residue on the finger. The time at which this occurs is referred to a the tack-free time. The rise times of these foams were determined by the movement of a slide wire which rests on a piece of aluminum foil on the surface of the foam. The rise time is called when the slide wire rises less than a millimeter in a 5 second interval.

CONVENTIONAL FLEXIBLE FOAMS USING SILOXYLATED TIN CATALYSTS

The catalyst of this invention produced acceptable quality, well cured foam with desired cream-rise profiles. Tables VI thru XII shows the evaluation of the siloxylated organometallic catalyst in both high and low water formulations. In this type of formulation sixoxylated tin II compounds produced more open foam than T-9, and rise times of these foams were longer than control foam. However, these producet with longer rise times had similar gel times to control (Table VI). Tetravalent tin had a flat response to breathability and longer rise time profiles than control foams.

Tables VI, VII, VIII and XII show the different use levels of siloxylated di-or tetravalent tin compound in urethane foam. Foams α98, 99, 100 were made with siloxylated tin compounds. The activity of these products was approximately 25% higher than the control T-9 and T-12.

In Table XII, experimental product "G" was evaluated. This product produced lower density, higher breathability foams than control T-9 (foams 116 thru 118).

TABLE IV

| Foam | Evaluation of Metalosiloxane Catalyst In Polyurethane Foam | | | | | | | | | | | |
|---|---|---|---|---|---|---|---|---|---|---|---|---|
| | 21 | 22 | 23 | 24 | 25 | 26 | 27 | 28 | 29 | 30 | 31 | 32 |
| Polyol C | 100 | → | → | → | → | → | → | → | → | → | → | → |
| H$_2$O | 1.5 | → | → | → | → | → | → | → | → | → | → | → |
| | | | | | | See Below | | | | | | |
| Amine Catalyst | Varied | → | → | → | → | → | → | → | → | → | → | → |

TABLE IV-continued
Evaluation of Metalosiloxane Catalyst In Polyurethane Foam

| Foam | 21 | 22 | 23 | 24 | 25 | 26 | 27 | 28 | 29 | 30 | 31 | 32 |
|---|---|---|---|---|---|---|---|---|---|---|---|---|
| Trichloromonofluoromethane | 45 | → | → | → | → | → | → | → | → | → | → | → |
| Surfactant B | 2.0 | → | → | → | → | → | → | → | → | → | → | → |
| Catalyst | * | → | → | "E" | → | → | → | → | → | → | → | → |
| Conc. PHP. | 2.0 | | | 0.1 | | | 0.2 | → | → | 0.3 | → | → |
| Cream Time (sec) | 12 | 12 | 10 | 18 | 20 | 20 | 16 | 18 | 16 | 14 | 15 | 14 |
| Gel Time (sec) | 65 | 60 | 58 | 80 | 80 | 82 | 60 | 70 | 60 | 60 | 60 | 60 |
| Tack Free (sec) | 75 | 70 | 76 | 120 | 120 | 121 | 100 | 105 | 105 | 90 | 80 | 82 |
| Foam Density lb/ft³ | | 1.45 | | | 1.055 | | 1.139 | 1.130 | | 1.117 | | |

Polyol C — sucrose-amine polyol, autocatalytic, OH number 400, viscosity at 25° C. ± 14,500 cP
Surfacant B; non-hydrolyzable silicone surfacant
*Commercial Tertiary Amine Catalyst for rigid foam.

TABLE V
Evaluation of Metalsiloxane Catalyst in Rigid Polyurethane Foam

| Foam | 33 | 34 | 35 | 36 | 37 | 38 | 39 | 40 | 41 | 43 | 43 | 44 | 45 | 46 |
|---|---|---|---|---|---|---|---|---|---|---|---|---|---|---|
| Polyol C | 100 | → | → | → | → | → | → | → | → | → | → | → | → | → |
| H₂O | 1.5 | → | → | → | → | → | → | → | → | → | → | → | → | → |
| Amine Catalyst | Varied | → | → | → | → | → | See Below | → | → | → | → | → | → | → |
| Trichloromonofluoromethane | 45 | → | → | → | → | → | → | → | → | → | → | → | → | → |
| Surfactant B | 2.0 | → | → | → | → | → | → | → | → | → | → | → | → | → |
| TDR Index | 105 Index | → | → | → | → | → | → | → | → | → | → | → | → | → |
| Catalyst | "E" | → | → | → | → | → | J | → | → | G | → | → | → | → |
| Conc PHR | 0.4 | → | → | 0.5 | → | → | 0.1 | 0.05 | 0.15 | 0.1 | 0.2 | 0.3 | 0.4 | 0.5 |
| Cream Time (sec) | 13 | 13 | 12 | 10 | 12 | 10 | 15 | 12 | 14 | 18 | 16 | 15 | 14 | 12 |
| Gel Time (sec) | 57 | 55 | 55 | 57 | 55 | 56 | 62 | 60 | 50 | 65 | 55 | 50 | 45 | 45 |
| Tack Free (sec) | 75 | 80 | 78 | 72 | 74 | 72 | 68 | 72 | 75 | 110 | 100 | 80 | 80 | 80 |
| Foam Density lb/ft³ | 1.135 | 1.124 | 1.150 | 1.457 | 1.350 | 1.252 | 1.135 | 1.124 | 1.156 | 1.257 | 1.250 | 1.153 | 1.211 | 1.051 |

The free rise bench foams used in this work were prepared from commercial grade materials according to the specified formulations outlined in the data tables. The general procedure for the preparation and testing of foam is described briefly.

In the case of flexible foam, a one-quart cardboard cup is charged with polyol. The surfactant is then weighed in and blended into the polyol with a wooden tongue depressor. The water and amine are added as a premixed solution. A baffle is then inserted into the cup and the mixture is blended with an ether blade, attached to a drill press, spinning at 200 rpm for a period of 15 seconds. The tin catalyst is added via syringe, blended with the drill press for 7 seconds, and a weighed aliquot of TDI is poured in rapidly, without interrupting the stirring. Stirring is continued for a total of 15 seconds, then stopped and the formulation is poured into a 12"×12"×12" cardboard box. Rise times were measured by the blow off of excess carbon dioxide or by measuring the movement of a slide wire supported by a piece of aluminum foil on the top of the foam. After the foaming reaction was completed the foams were oven cured for 10 minutes at 125° C. and allowed to cool to room temperature overnight before being cut.

TABLE VI
Conventional Flexible Urethane Foam
3.8 pt H₂O/0.23 pt Amine A/1.6 pt Surfactant C

| Foam | Metal Catalyst | Concentration | Cream Time | Rise Time | Gel Time | Top Coll. | Split | Hgt Rise | Nopco | Density |
|---|---|---|---|---|---|---|---|---|---|---|
| 47 | T-9 | 0.18 | 10/11 | 94 | 102 | — | None | 8.6 | 5.5 | 1.51 |
| 48 | | 0.24 | ↓ | 86 | 94 | +0.05 | None | 8.9 | 4.25 | 1.52 |
| 49 | | 0.275 | ↓ | 82 | 90 | +0.1 | None | 9.3 | 2.75 | 1.51 |
| 50 | "E" | 0.18 | 10/11 | 80 | 88 | +0.05 | None | 9.5 | 2.75 | 1.45 |
| 51 | | 0.24 | ↓ | 76 | 83 | +0.1 | None | 9.4 | 2.5 | 1.44 |
| 52 | | 2.75 | ↓ | 74 | 81 | +0.1 | None | 9.4 | 2.75 | 1.43 |
| 53 | "I" | 0.18 | 10/11 | 107 | 118 | −.05 | | 8.3 | 6.0 | 1.55 |
| 54 | | 0.275 | ↓ | 106 | 114 | +.05 | | 8.3 | 5.5 | 1.52 |
| 55 | "H" | 0.18 | 10/11 | 105 | 114 | | None | 8.4 | 5.5 | 1.52 |
| 56 | | 0.275 | ↓ | 102 | 111 | +.05 | | 8.4 | 5.5 | 1.57 |

T-9: Stannous Octoate
T-12: dibutyltindiluarate
Amine A: 33 wt % triethylenediamine and 67 wt % dipropylene glycol solvent
Surfactant C: hydrolyzable silicone surfacant

TABLE VII
Conventional Flexible Polyurethane Foam
(4.63 pt H₂O/0.17 pt Amine A/1.1 pt Surfactant C)

| Foam | Metal Catalyst | Concentration | Cream Time | Rise Time | Gel Time | Top Coll. | Split | Hgt Rise | Nopco | Density |
|---|---|---|---|---|---|---|---|---|---|---|
| 57 | T-9 | 0.17 | 10/11 | 101 | 110 | — | None | 10.9 | 5.5 | 1.33 |
| 58 | | 0.2 | ↓ | 88 | 96 | +.05 | None | 11.0 | 5.25 | 1.33 |
| 59 | | 0.23 | ↓ | 83 | 90 | +.1 | None | 11.3 | 4.5 | 1.27 |

TABLE VII-continued

Conventional Flexible Polyurethane Foam
(4.63 pt H$_2$O/0.17 pt Amine A/1.1 pt Surfactant C)

| Foam | Metal Catalyst Concentration | | Cream Time | Rise Time | Gel Time | Top Coll. | Split | Hgt Rise | Nopco | Density |
|---|---|---|---|---|---|---|---|---|---|---|
| 60 | "I" | 0.17 | 10/11 | 113 | 123 | −.2 | None | 10.3 | 7.0 | 1.4 |
| 61 | | 0.2 | ↓ | 106 | 127 | −.01 | None | 10.3 | 6.0 | 1.39 |
| 62 | | 0.23 | ↓ | 100 | 110 | — | None | 10.6 | 5.0 | 1.28 |
| 63 | "H" | 0.17 | ↓ | 102 | 124 | −.15 | None | 10.2 | 8.0 | 1.36 |
| 64 | | 0.2 | ↓ | 77 | 109 | — | | 10.5 | 6.8 | 1.28 |
| 65 | | 0.23 | ↓ | 89 | 100 | — | | 10.9 | 5.5 | 1.32 |

TABLE VIII

Conventional Flexible Polyurethane Foam
(4.63 pt H$_2$O/0.1 pt Amine B/1.1 pt Surfactant C)

| Foam | Metal Catalyst Concentration | | Cream Time | Rise Time | Gel Time | Top Coll. | Split | Hgt Rise | Nopco | Density |
|---|---|---|---|---|---|---|---|---|---|---|
| 66 | T-9 | 0.17 | 10-11 | 92 | 102 | −.05 | None | 10.8 | 6.0 | 1.34 |
| 67 | | 0.2 | ↓ | 87 | 97 | — | | 11.3 | 4.5 | 1.33 |
| 68 | | 0.23 | ↓ | 81 | 91 | +.05 | | 11.6 | 2.5 | 1.32 |
| 69 | T-12 | 0.17 | ↓ | 81 | 91 | — | | 11.1 | 4.0 | 1.31 |
| 70 | | 0.2 | ↓ | 77 | 87 | .05 | | 11.7 | 3.25 | 1.30 |
| 71 | | 0.23 | ↓ | 77 | 84 | +.1 | | 11.7 | 3.0 | 1.30 |
| 72 | "E" | 0.17 | ↓ | 76 | 86 | — | | 11.4 | 4.0 | 1.28 |
| 73 | | 0.2 | ↓ | 74 | 84 | +.05 | | 11.8 | 4.0 | 1.28 |
| 74 | | 0.23 | ↓ | 73 | 83 | +.1 | | 11.7 | 3.0 | 1.29 |
| 75 | "I" | 0.17 | ↓ | 114 | 124 | — | | 10.1 | 7.25 | 1.38 |
| 76 | | 0.2 | ↓ | 109 | 119 | — | | 10.4 | 6.5 | 1.37 |
| 77 | | 0.23 | ↓ | 101 | 111 | — | | 10.7 | 5.5 | 1.35 |
| 78 | "H" | 0.17 | ↓ | 105 | 115 | −0.2 | | 10.2 | 6.5 | 1.39 |
| 79 | | 0.2 | ↓ | 99 | 109 | −.05 | | 11.0 | 6.0 | 1.35 |
| 80 | | 0.23 | ↓ | 91 | 101 | — | | 11.0 | 5.25 | 1.31 |

Amine B: water-soluble, low odor mixture of amine catalyst

TABLE IX

Conventional Flexible Polyurethane Foam
(3.8 pt H$_2$O/0.14 pt Amine B/1.6 pt Surfactant C)

| Foam | Metal Catalyst Concentration | | Cream Time | Rise Time | Gel Time | Top Coll. | Split | Hgt Rise | Nopco | Density |
|---|---|---|---|---|---|---|---|---|---|---|
| 81 | T-9 | 0.23 | 10/11 | 100 | 108 | — | None | 8.9 | 6.2 | 1.5 |
| 82 | | 0.275 | ↓ | 91 | 98 | +.05 | | 9.0 | 4.9 | 1.53 |
| 83 | | 0.32 | ↓ | 83 | 90 | +.1 | | 9.2 | 3.4 | 1.47 |
| 84 | T-12 | 0.23 | ↓ | 94 | 99 | +.1 | | 8.8 | 5.0 | 1.45 |
| 85 | | 0.275 | ↓ | 90 | 98 | +.10 | | 9.2 | 4.5 | 1.47 |
| 86 | | 0.32 | ↓ | 85 | 90 | +.15 | | 9.3 | 3.0 | 1.45 |
| 87 | "E" | 0.23 | ↓ | 92 | 99 | — | Small side | 9.0 | 4.6 | 1.5 |
| 88 | | 0.275 | ↓ | 88 | 96 | +.1 | Small side | 9.3 | 4.6 | 1.45 |
| 89 | | 0.32 | ↓ | 86 | 96 | +.1 | None | 9.5 | 5.0 | 1.42 |
| 90 | "I" | 0.23 | ↓ | 88 | 96 | +.1 | None | 8.9 | 4.5 | 1.5 |
| 91 | | 0.275 | ↓ | 84 | 91 | +.1 | | 9.1 | 3.0 | 1.49 |
| 92 | | 0.32 | ↓ | 80 | 85 | +.15 | | 9.5 | 1.55 | 1.46 |
| 93 | "H" | 0.23 | ↓ | 98 | 106 | +.1 | | 8.6 | 7.0 | 1.51 |
| 94 | | 0.275 | ↓ | 94 | 101 | +.1 | | 9.0 | 5.5 | 1.52 |
| 95 | | 0.32 | ↓ | 91 | 97 | +.15 | | 9.0 | 5.0 | 1.52 |

TABLE X

Conventional Flexible Polyurethane Foam

| Foam | 96 | 97 | 98 | 99 | 100 | 101 | 102 | 103 | 104 | 405 |
|---|---|---|---|---|---|---|---|---|---|---|
| Polyol D | 100. | 100. | 100. | 100. | 100. | 100. | 100. | 100. | 100. | 100. |
| H$_2$O | 4.63 | 4.63 | 4.63 | 4.63 | 4.63 | 4.63 | 4.63 | 4.63 | 4.63 | 4.63 |
| Amine A | 0.17 | 0.17 | 0.17 | 0.17 | 0.17 | — | — | — | — | — |
| Amine B | — | — | — | — | — | 0.1 | 0.1 | 0.1 | 0.1 | 0.1 |
| Surfactant C | 1.1 | 1.1 | 1.1 | 1.1 | 1.1 | 1.1 | 1.1 | 1.1 | 1.1 | 1.1 |
| T-9 | 0.2 | — | — | — | — | 0.2 | — | — | — | — |
| T-12 | — | 0.2 | — | — | — | — | 0.2 | — | — | — |
| "E" | — | — | 0.15 | — | — | — | — | 0.15 | — | — |
| "I" | — | — | — | 0.15 | — | — | — | — | 0.15 | — |
| "H" | — | — | — | — | 0.15 | — | — | — | — | 0.15 |
| TDI 80/20 | 61.2 | 61.2 | 61.2 | 61.2 | 61.2 | 61.2 | 61.2 | 61.2 | 61.2 | 61.2 |
| Gel Time (sec) | 95 | 92 | 86 | 90 | 98 | 94 | 89 | 88 | 89 | 97 |
| Cream Time (sec) | 10-11 | 10-11 | 10-11 | 10-11 | 10-11 | 10-11 | 10-11 | 10-11 | 10-11 | 10-11 |
| Rise Time (sec) | 87 | 84 | 77 | 82 | 90 | 86 | 81 | 80 | 81 | 89 |

TABLE X-continued

| | Conventional Flexible Polyurethane Foam | | | | | | | | | |
|---|---|---|---|---|---|---|---|---|---|---|
| Foam | 96 | 97 | 98 | 99 | 100 | 101 | 102 | 103 | 104 | 405 |
| Top Collapse (inches) | −.1 | +.15 | +.1 | +.15 | +.1 | +.1 | +.25 | +.15 | +.15 | +.1 |
| Amb. Temp. °F. | 71 | 71 | 71 | 71 | 70 | 71 | 71 | 71 | 71 | 71 |
| Height of Rise (inches) | 11.1 | 11.4 | 11.8 | 11.7 | 10.9 | 11.2 | 11.4 | 11.6 | 11.6 | 11.2 |
| Breathability (SCFM) | 4.6 | 2.8 | 2.3 | 2.5 | 5.6 | 4.8 | 4.3 | 4.3 | 2.5 | 5.5 |
| Cells per inch | 35–40 | 35–40 | 35–40 | 35–40 | 35–40 | 35–40 | 35–40 | 35–40 | 35–40 | 35–40 |
| Density, PCF | 1.32 | 1.28 | 1.27 | 1.29 | 1.31 | 1.33 | 1.27 | 1.28 | 1.28 | 1.32 |
| Density PCF Core | 1.34 | 1.29 | 1.27 | 1.31 | 1.34 | 1.33 | 1.3 | 1.31 | 1.27 | 1.36 |
| Tensile, lbs. | 4.2 | 4.6 | 4.53 | 4.16 | 3.9 | 4.2 | 4.5 | 4.4 | 4.0 | 3.93 |
| Elongation, lbs | 3.10 | 3.92 | 3.66 | 2.93 | 3.05 | 3.075 | 3.0 | 3.57 | 2.57 | 2.72 |
| Tear, lbs. | 2.0 | 2.4 | 2.3 | 1.6 | 1.9 | 1.9 | 2.0 | 2.4 | 2.2 | 1.8 |
| 90% Comp. % loss | 8.2 | 17.3 | 15.8 | 14.7 | 5.7 | 8.6 | 9.6 | 9.7 | 13.03 | 7.7 |
| IFD 25 | 45 | 40 | 40 | 49 | 40 | 45 | 39 | 38 | 49 | 43 |
| 65 | 79 | 70 | 78 | 88 | 70 | 80 | 69 | 66 | 88 | 76 |
| 25% Return | 31 | 28 | 27 | 33 | 28 | 31 | 27 | 26 | 33 | 29 |
| Load Ratio | 1.75 | 1.75 | 1.95 | 1.29 | 1.75 | 1.77 | 1.76 | 1.73 | 1.79 | 1.76 |

Polyol D: 3000 molecular weight triol, OH number 56

TABLE XI

| | Conventional Flexible Polyurethane Foam | | | | | | | | | |
|---|---|---|---|---|---|---|---|---|---|---|
| Foam | 106 | 107 | 108 | 109 | 110 | 111 | 112 | 113 | 114 | 115 |
| Polyol D | 100. | 100. | 100. | 100. | 100. | 100. | 100. | 100. | 100. | 100. |
| $H_2O$ | 3.8 | 3.8 | 3.8 | 3.8 | 3.8 | 3.8 | 3.8 | 3.8 | 3.8 | 3.8 |
| Amine A | 0.23 | 0.23 | 0.23 | 0.23 | 0.23 | — | — | — | — | — |
| Amine B | — | — | — | — | — | 0.14 | 0.14 | 0.14 | 0.14 | 0.14 |
| Surfactant C | 1.6 | 1.6 | 1.6 | 1.6 | 1.6 | 1.6 | 1.6 | 1.6 | 1.6 | 1.6 |
| T-9 | 0.275 | — | — | — | — | 0.275 | — | — | — | — |
| T-12 | — | 0.275 | — | — | — | — | 0.275 | — | — | — |
| "E" | — | — | 0.2 | — | — | — | — | 0.2 | — | — |
| "I" | — | — | — | 0.2 | — | — | — | — | 0.2 | — |
| "H" | — | — | — | — | 0.2 | — | — | — | — | 0.2 |
| TDI 80/20 (105) | 47.8 | 47.8 | 47.8 | 47.8 | 47.8 | 47.8 | 47.8 | 47.8 | 47.8 | 47.8 |
| Gel Time (sec.) | 96 | 93 | 98 | 92 | 101 | 93 | 92 | 93 | 88 | 101 |
| Cream Time (sec.) | 10–11 | 10–11 | 10–11 | 10–11 | 10–11 | 10–11 | 10–11 | 10–11 | 10–11 | 10–11 |
| Rise Time (sec.) | 89 | 86 | 91 | 85 | 94 | 86 | 85 | 86 | 81 | 94 |
| Top Collapse (inches) | +.1 | +.2 | +.2 | +.2 | +.1 | +.1 | +.15 | +.1 | +.1 | +.1 |
| Amb. Temp. °F. | 71 | 71 | 71 | 71 | 71 | 72 | 71 | 72 | 72 | 72 |
| Height of Rise (inches) | 8.8 | 9.0 | 9.4 | 9.1 | 8.7 | 8.8 | 8.8 | 9.2 | 9.1 | 8.7 |

TABLE XII

| Ingredients | 116 | 117 | 118 |
|---|---|---|---|
| Polyol E | 100 | → | → |
| $H_2O$ | 4.1 | → | → |
| Catalyst AA | | | |
| Silicone Surfactant | 1.0 | → | 1.0 |
| Trichlorofluoromethane | 5.0 | | |
| T-9 | .25 | → | |
| "G" | | .25 | → |
| TDI 80/82 | 48.3 | → | → |
| Top Collapse | .7" | .6" | .7" |
| Rise Time | 92 sec. | 77 sec. | 77 sec. |
| HT, Rise | 26.1" | 27.8" | 28.8" |
| Breathability (Nopco) | 3.00 | 4.55 | 4.85 |
| Density Pounds/ft³ | 1.34 | 1.25 | 1.29 |
| SAC Factor | 1.93 | 1.90 | 1.90 |

What is claimed is:

1. A process for preparing a siloxylated organometallic catalyst which comprises reacting below 100° C. a silylamine of the formula:

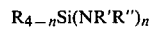

wherein R is a alkyl, alkaryl, alkenyl, alkynyl, aryl cycloaliphatic, or heteroatom substituted aliphatic siloxy or substituted siloxy group; R' and R" are individually hydrogen, alkyl, alkenyl, alkynyl, aryl, cycloaliphatic, or heteroatom substituted aliphatic, groups provided R' and R" cannot both be hydrogen; and n is one to four inclusive, with a metallic carboxylate of the formula:

wherein M is a metal with an oxidation state, R''' and R'''' are individually an alkyl, alkaryl, alkenyl, alkynyl, aryl, cycloaliphatic, or heteroatom substituted aliphatic, group; x is at least one but no more than the oxidation state of M and y is equal to the oxidation state of M minus x, and M is greater than or equal to two.

2. The process of claim 1 wherein the R, R' and R" groups of the silylamine employed are alkyl groups containing no more than twenty-four carbon atoms each.

3. The process of claim 2 wherein the R, R' and R" groups of the silylamine employed contain no more than twelve carbons each.

4. The process of claim 3 where in the R, R' and R" groups of the silylamine employed are methyl groups.

5. The process of claim 1 wherein the value of n is equal to one.

6. The process of claim 1 wherein the R''' and R'''' groups of the metallic carboxylate are alkyl groups containing no more than twenty-four carbon atoms each.

7. The process of claim 6 wherein the R''' and R'''' groups of the metallic carboxylate contain no more than twelve carbon atoms.

8. The process of claim 1 wherein M is a metal selected from the group consisting of the metals of group IB, IIB, IIIB, IVB, VB, VIB, VIIB, VIII, gallium, indium, thallium, germanium, tin and lead.

9. The process of claim 8 wherein M is selected from the group consisting of iron, tin, lead, titanium, cerium and mercury.

* * * * *